(12) United States Patent
Boyle et al.

(10) Patent No.: US 6,257,051 B1
(45) Date of Patent: Jul. 10, 2001

(54) ON-BOARD ROTATIONAL VISCOMETERS

(75) Inventors: Frederick P. Boyle, Kirtland; Gary Garvin, Mentor; Klaus-Werner Damm, Chagrin Falls; Daniel H. Heath, Ravenna; Herman F. George, Chardon, all of OH (US); Peter John Moore, Hampshire (GB); Dale Hicks, Surrey (GB); Terence Edward Robinson, Hampshire (GB)

(73) Assignee: The Lubrizol Corporation, Wickliffe, OH (US)

( * ) Notice: Subject to any disclaimer, the term of this patent is extended or adjusted under 35 U.S.C. 154(b) by 0 days.

(21) Appl. No.: 09/268,504

(22) Filed: Mar. 11, 1999

(51) Int. Cl.[7] .............................. G01N 11/00; G01N 11/14
(52) U.S. Cl. .......................................... 73/54.01; 73/54.35
(58) Field of Search ............................... 73/54.01, 54.23, 73/54.27, 54.33, 54.35

(56) References Cited

U.S. PATENT DOCUMENTS

| 2,468,370 | 4/1949 | Källe .................................... 73/54 |
| 3,572,086 | 3/1971 | Johnston et al. ........................ 73/59 |
| 4,466,276 | 8/1984 | Ruyak et al. ........................... 73/59 |
| 4,499,753 | * 2/1985 | Carr ................................... 73/54.35 |
| 4,524,611 | 6/1985 | Richon et al. .......................... 73/59 |
| 4,557,142 | 12/1985 | Hensley et al. ....................... 73/153 |
| 4,643,020 | * 2/1987 | Heinz .................................. 73/54.27 |
| 4,736,624 | 4/1988 | Arnstein et al. ........................ 73/59 |
| 5,167,143 | 12/1992 | Brookfield ........................... 73/54.23 |
| 5,315,864 | 5/1994 | Surjaatmadja et al. .............. 73/54.32 |
| 5,394,739 | * 3/1995 | Garvey, III et al. ................ 73/54.23 |
| 5,609,275 | 3/1997 | Brown et al. .......................... 222/413 |
| 5,763,766 | * 6/1998 | Robinson ............................ 73/54.33 |

FOREIGN PATENT DOCUMENTS

| 007 427 | 6/1979 | (EP) . |
| 399 634 | 1/1990 | (EP) . |
| 2 188 162 | 1/1986 | (GB) . |
| 08138178 | 12/1997 | (JP) . |

OTHER PUBLICATIONS

Tuthill Magnetic Drive Gear Pumps catalogue.

* cited by examiner

*Primary Examiner*—Hezron Williams
*Assistant Examiner*—Jay L. Politzer
(74) *Attorney, Agent, or Firm*—Teresan W. Gilbert; Michael F. Esposito

(57) ABSTRACT

A viscometer for sensing or characterizing the stress required to shear a fluid at a given rate includes a pair of members coaxially mounted for relative rotation. Between the members is an annular gap defining a flow path for the fluid. The flow path is configured such that during differential rotation of the members, fluid is caused to flow through the annular gap that is a function of the differential rotation and the viscosity of the fluid. A sensor measures the torque or torque equivalent required to achieve such differential rotation between the members.

23 Claims, 3 Drawing Sheets

ON-BOARD ROTATIONAL VISCOMETERS

FIELD OF THE INVENTION

This invention relates to viscometers used to measure or characterize the stress needed to shear a fluid at a given rate. In particular, this invention relates to viscometers for continuously monitoring changes in the viscosity of fluids used in or produced by a device or process including low-viscosity fluids such as engine lubricants, by monitoring the torque required to achieve differential rotation between two elements defining a flow path for the fluid there between. Such viscometers may be used for example in on-board systems to maintain the quality of engine lubricants which is essential to the proper operation and long service life of internal combustion engines or other equipment.

BACKGROUND OF THE INVENTION

One common form of viscometer comprises two coaxial cylinders (cylinder-in-cylinder) which are rotated relative to one another while measuring, either visually or electronically, the torque, or torque equivalent, required to achieve a differential rotation speed. The flow characteristics of the fluid can be determined by interposing the fluid in an annular gap between the cylinders and for a known differential rotational speed, measuring the torque, or torque equivalent. By factoring in the physical dimensions and the drag associated with bearings or seals of the viscometer that can affect torque measurement, the viscosity of the fluid can be calculated for a particular shear rate. Typically, a viscometer is driven at a single speed and the viscosity calculated at a single shear rate to allow relative comparison of fluids. However, if desired the viscometer can also be used to more fully characterize a fluid, by measuring torque over a range of differential rotational speeds.

In certain applications, viscometers are used to continuously monitor a fluid used in or produced by a device or process. The fluids can be either totally liquid or a liquid containing particulate. One method for using known coaxial cylinder viscometers in these applications is to put the viscometers in line with the fluid flow. Problems with this method include the complexity of designing the viscometers into the flow circuit, the difficulty in replacing components of the viscometers should failure occur, and accuracy issues should the fluid flow past the viscometers vary from a constant rate.

One way of overcoming some of the problems associated with mounting cylinder-in-cylinder viscometers in line with the flow path is to mount the viscometers outside the main flow path. In this arrangement, the outer cylinder of the viscometers is capped to form a cup-like structure with the inner cylinder or bob inside the cup. This allows the drive for the differential rotation to be mounted quite close to the rotating elements for a more compact design and also allows maintenance issues to be more easily addressed.

A problem with prior bob-in-cup viscometers used to continuously monitor a fluid used in or produced by a device or process is that a pump or other hardware is needed to control the fluid flow through the viscometers, which adds to the cost and complexity of using the viscometers. Another problem with prior bob-in-cup viscometers is that, when used to accurately measure low viscosity fluids containing particulate, particulate settling can occur resulting in inaccurate viscosity calculation. Thus, careful placement of prior bob-in-cup viscometers is critical to proper operation. Also, such viscometers are potentially subject to a number of possible sources of error due to unwanted friction and/or drag effects.

SUMMARY OF THE INVENTION

The present invention overcomes the above-noted and other shortcomings of prior bob-in-cup viscometers by providing a relatively simple way of continuously monitoring fluid viscosity without the cost and complexity of a pump or other hardware to maintain flow through the viscometers, and without the placement issues normally needed to prevent particulate settling when measuring particulate-containing low-viscosity fluids.

In accordance with one aspect of the invention, the viscometers are self pumping in order to maintain controlled fluid flow through the sections of the viscometers where the fluid flow properties are measured, essentially independent of flow rate of the fluid through its primary flow path. The self-pumping character of the viscometers is also a benefit in preventing particulate settling when used to accurately measure relatively low viscosity (e.g., 1 to 100 cSt.) fluids that may contain finely, relatively well-dispersed solids.

In accordance with another aspect of the invention, the viscometer bobs and cups are designed such that relative rotation between the two elements urges the fluid to flow through the viscometers due to a pressure differential caused by the rotation.

In accordance with another aspect of the invention, the flow through the viscometers is both controlled and sufficient to minimize or eliminate clogging due to any particulate settling from the fluid.

In accordance with another aspect of the invention, in one embodiment, the bob comprises a hollow cylinder closed at one end adjacent the closed end of the cup and open at the other end. Extending through the wall of the bob at a location near its closed end and facing a continuous wall of the cup are a plurality of discrete circumferentially spaced openings. Differential bob/cup rotation urges fluid from a volume outside the bob through the bob and out through the discrete openings in the bob wall for passage through an annular gap between the bob and cup and into a volume outside the cup.

In accordance with another aspect of the invention, in another embodiment, a plurality of discrete circumferentially spaced openings are provided in the wall of the cup near the closed end of the cup facing a continuous wall of the bob. Differential bob/cup rotation urges fluid from the volume outside the bob, through the annular gap between the cup and bob and out through the discrete openings of the cup wall to a volume outside the cup.

In accordance with another aspect of the invention, in another embodiment, the wall of the bob has discrete circumferentially spaced openings near one end facing a continuous wall of the cup, and the cup has discrete circumferentially spaced openings facing a continuous wall of the bob near the end of the bob that is opposite the end of the bob containing discrete openings. Differential bob/cup rotation urges fluid from a volume outside the bob through the discrete wall openings of the bob and annular gap between the bob and cup and out through the discrete openings in the cup to a volume outside the cup.

In accordance with another aspect of the invention, in another embodiment, the bob is a cylinder of finite side wall thickness open at both ends. Also, one of the open ends is spaced from the closed end of the cup an axial distance of between one half to five times the radial separation between the bob and cup, whereby differential bob/cup rotation urges fluid from a volume outside the bob through the bob, the separation between the end of the bob and closed end of the cup, and the annular gap between the bob and cup and into a volume outside the cup.

In accordance with another aspect of the invention, in another embodiment, a series of alternate coaxial cylinders of finite wall thickness are alternately supported by a pair of axially spaced end plates to provide alternate coaxial bobs and cups. One end plate has a central opening providing fluid communication between a volume outside the end plate and the center cylinder. Discrete circumferentially spaced openings are provided through the cylindrical wall of at least one bob/cup near its open end facing a continuous cylindrical wall of an adjacent cup/bob. Differential rotation of the end plates urges fluid from a volume outside the viscometer through the center cylinder and separations between the bob/cup cylinders and opposed end plates and through the circumferentially spaced openings in at least one bob/cup cylinder and the annular gaps between adjacent bob/cup cylinders and out through the annular gap between the last two bob/cup cylinders into the volume outside the viscometer.

In accordance with another aspect of the invention, in another embodiment, the separation between the end of at least one of a plurality of coaxial bob/cup cylinders and the opposed end plate is between one half to five times the annular gap between adjacent bob/cup cylinders. Differential rotation of the end plates urges fluid from a volume outside the viscometer through the center bob and separations between the bob/cup cylinders and opposed end plates and through the annular gaps between adjacent bob/cup cylinders and out through the annular gap between the last two bob/cup cylinders into the volume outside the viscometer.

In accordance with another aspect of the invention, in another embodiment, the bob and cup are axially symmetric but non-cylindrical. Also, the bob has a coaxial bore extending all the way through the bob, and an annular gap is provided between the bob and cup that either remains the same or increases as a function of radius from the common axis of the bob and cup. Differential bob/cup rotation urges fluid from a volume outside the bob through the coaxial bore of the bob, through the gap between the bob and cup and into the volume outside the cup.

In accordance with another aspect of the invention, a magnetic drive coupling is provided between the rotating element of the viscometer and the viscometer drive motor.

In accordance with another aspect of the invention, in one embodiment, the rotating element is the driven magnet of the magnetic drive coupling and is surrounded by the driving magnet, allowing the rotating element to self-locate centrally in the magnetic field of the driving magnet, thus eliminating the need for end thrust location of the rotating element, which is a possible source of error due to friction on the thrust faces.

In accordance with another aspect of the invention, the rotating element is mounted on a hollow shaft which permits fluid from a volume outside the rotating element to pass through the rotating element into a separation between the end of the rotating element and the closed end of a relatively fixed cup. Rotation of the rotating element within the cup urges fluid from a volume outside the rotating element through the rotating element and separation between the end of the rotating element and closed end of the cup and through the annular gap between the cup and rotating element and into a volume outside the cup.

In accordance with another aspect of the invention, the portion of the viscometer housing carrying bearing bushes for the rotating shaft is provided with radial holes to reduce the friction effect caused by fluid between the rotating shaft and housing in order to reduce unwanted drag effects.

In accordance with another aspect of the invention, in another embodiment, the driven magnet is mounted on the bottom side of the viscometer bob and is polarized north and south from one side to the other for magnetic coupling with a driving magnet on the rotor shaft.

In accordance with another aspect of the invention, a bob shaft is pressed into an axial hole in the bob and has radiuses at both ends slightly smaller than half ball radiuses in insert bearings in which the bob shaft ends are received to cause the bob to move like a gyro with little effort required.

In accordance with another aspect of the invention, end play between the bob shaft and insert bearings is preferably no more than 0.010 inch, whereby the viscometer may operate in any position.

In accordance with another aspect of the invention, a plurality of circumferentially spaced slots are provided in the side of the cup in line with the cup bottom to allow debris and sediment entering the annular gap between the cup and bob to exit the cup and allow free flow of fluid through such annular gap.

To the accomplishment of the foregoing and related ends, the invention, then, comprises the features hereinafter fully described and particularly pointed out in the claims, the following description and the annexed drawings setting forth in detail certain illustrative embodiments of the invention, these being indicative, however, of but a few of the various ways in which the principles of the invention may be employed.

DETAILED DESCRIPTION OF THE PREFERRED EMBODIMENTS

The viscometers of the present invention are generally of the "bob-in-cup" type and are designed such that relative rotation between the bob and cup causes fluid flow through the viscometers due to a pressure differential created during rotation. The fluid flow through the viscometers is both controlled and sufficient to minimize or eliminate clogging due to any particulate settling from the fluid. Such viscometers are designed to detect small changes in the viscosity of low viscosity fluids such as engine lubricants, by monitoring the load imposed on a suited drive motor which may be a precision motor or a suited air motor.

Figure 1:
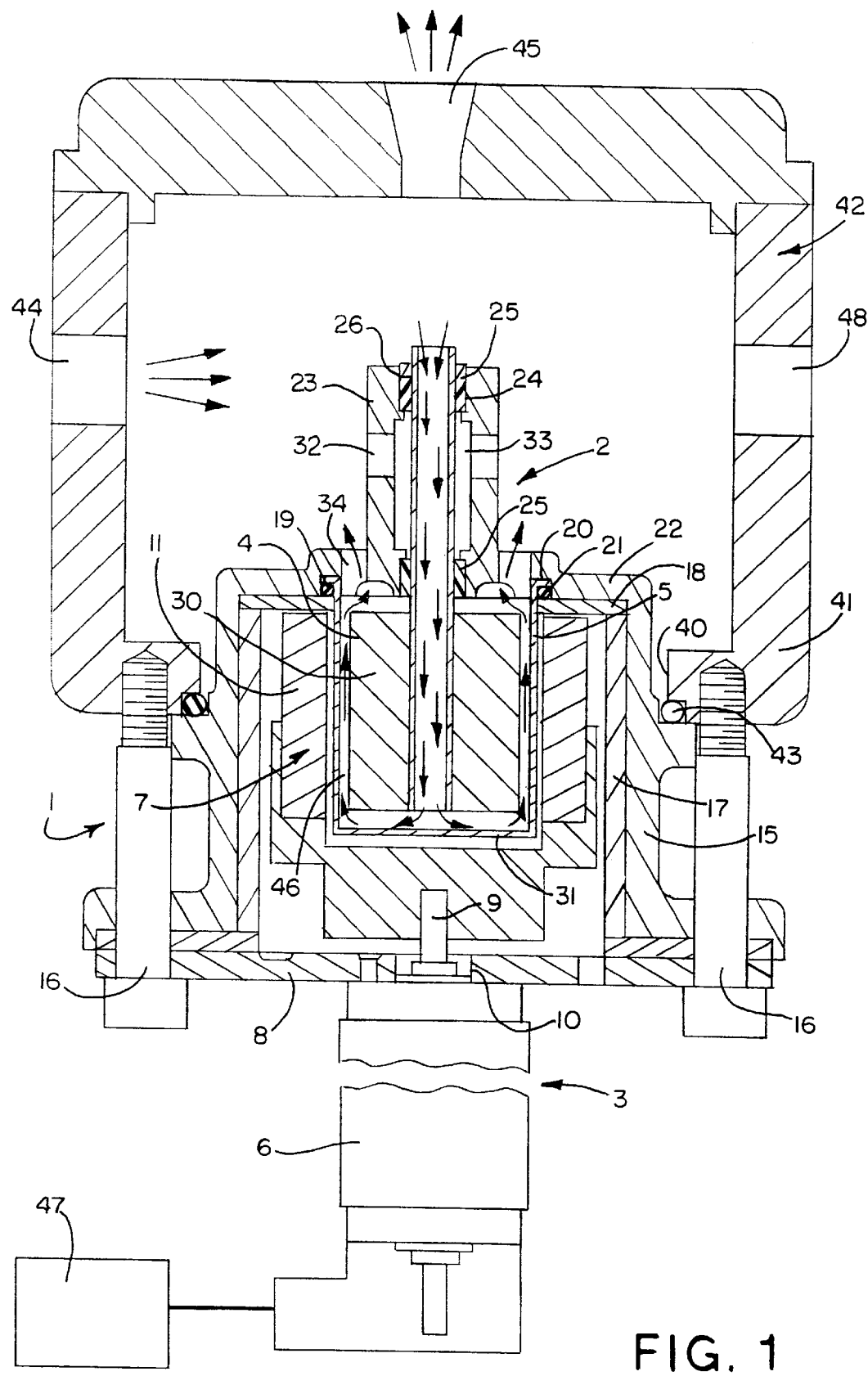
FIG. 1 is a fragmentary longitudinal section through one form of viscometer according to this invention.

FIG. 1 shows one such viscometer 1 in accordance with this invention which is constructed as a unit for in-line or diagnostic chamber mounting and includes two distinct sections, a sensing section 2 and a drive motor section 3. The sensing section 2 includes a coaxial bob 4 and cup 5, whereas the drive motor section 3 includes a suited drive motor 6 which in this case is a precision electric motor which preferably drives the bob 4 through a conventional magnetic drive coupling 7 as described hereafter.

In the embodiment shown in FIG. 1, the drive motor 6 is mounted to a locating plate 8 with its motor shaft 9 extending through an opening 10 in the plate. Attached to the motor shaft 9 is the driving magnet 11 of the magnetic drive coupling 7. Driving magnet 11 is cylindrical in shape and surrounds the cup 5 through which the fluid is continuously circulated during monitoring of the fluid.

The mounting plate 8 may be attached to the viscometer housing 15 by suitable fasteners 16 which, when tightened, cause the plate 8 to be pressed against one end of a sleeve 17. This forces the other end of the sleeve into engagement with a clamping ring 18 which in turn presses a ring seal 19 into sealing engagement with an outturned flange 20 on the cup received in an annular groove 21 in an end wall 22 of the viscometer housing to clamp and seal the cup to the viscometer housing.

Extending axially outwardly from the housing end wall 22 is a concentric hub portion 23 containing a longitudinal bore 24 concentric with the cup 5. Mounted within the bore 24 are spaced apart ball bearing 27 and bearing bush 25 for rotatably supporting one end of a hollow shaft 26 within the bore. The hollow shaft 26 extends into the cup 5 to provide a rotating support for the bob 4 in concentric spaced relation within the cup 5.

In the FIG. 1 embodiment, the bob 4 is the driven magnet 30 of the magnetic drive coupling 7 which is surrounded by the external driving magnet 11. The magnetic field of the external driving magnet 11 acts through the cup 5, causing the bob 4, which has a finite side wall thickness, to self-locate centrally within the cup 5 with the inner end of the bob spaced from the closed end 31 of the cup an axial distance that is between one half to five times the radial separation between the bob and cup. Such self-location of the bob 4 centrally within the magnetic field permits the bob shaft 26 to be installed in the bearing bushes 25 with no end thrust location on the shaft, thus removing a possible source of error due to friction on the thrust faces.

The hub portion 23 of the viscometer housing 15 carrying ball bearing 27 and bearing bush 25 has additional radial holes 32 communicating with an annular groove 33 in the wall of the bore 24 between the bearing and bush to reduce the friction effects caused by fluid between the rotating shaft 26 and hub 23 to reduce unwanted drag effects. This insures that the viscosity monitoring occurs along the annular gap between the rotating bob 4 and the fixed cup 5.

A series of circumferentially spaced holes 34 are provided in the end wall 22 of the viscometer housing 15 generally in line with the upper end of the rotating bob 4 to insure continuous flow of fluid through the viscometer.

The sensing section 2 of the viscometer 1 including the hub portion 23 extends through an opening 40 in the wall 41 of a diagnostic chamber 42 and may be clamped and sealed against a seal ring 43 between the viscometer housing 15 and diagnostics chamber wall 41 around the opening by the same fasteners 16 used to mount the motor plate 8 to the outwardly protruding end of the viscometer housing. Fluid enters and exits the diagnostics chamber 42 through suitable inlet and exit ports 44 and 45 in the wall of the chamber. This completely immerses the sensing section 2 of the viscometer in the fluid during operation of the viscometer 1, which occurs by energizing the drive motor 3 to drive the external cylindrical magnet 11. As the external cylindrical magnet 11 rotates, the magnetic field acts through the cup 5 and drives the inner magnet 30 (which in this case is the bob 4) and associated bob shaft 26 which runs in the fluid. Such differential bob/cup rotation creates a pumping action urging fluid from the diagnostics chamber 42 outside the bob 4 through the bob shaft 26, then through the separation between the inner end of the bob 4 and closed end of the cup 5, then through the annular gap 46 between the bob 4 and cup 5 and out through the exit ports 34 in the end wall 22 of the viscometer housing into the volume of fluid within the diagnostics chamber outside the cup thus insuring continuous flow of fluid across the viscometer.

Measurement of the resistance to rotation (drag) of the rotating element 30 (in this case the bob within the cup 5) caused by the presence of the fluid in the annular gap between the bob and cup enables the viscosity of the fluid to be continuously monitored.

The effects of viscosity change of the fluid have a direct affect on the motor 3 loading due to the change in drag between the relatively rotating bob and cup. The load variations which are a function of changes in viscosity are translated into motor speed or current variations which are monitored by the electronics and the controller 47 for the motor. These variations are calibrated against known viscosities and can be programmed into the electronic control system to detect very small changes in viscosity over the viscosity measurement range expected. Also, current limiting may be used to prevent any damage to the motor or equipment in unusually high viscosity or load conditions.

The viscometer housing 15 and locating plate 8 as well as the cup 5 are desirably made of stainless steel.

One or more other ports 48 may also be provided in the wall 41 of the diagnostics chamber 42 for use in inserting other types of sensors including dielectric sensors, temperature sensors and/or pressure sensors and the like for sensing other parameters of the fluid.

Figure 2:
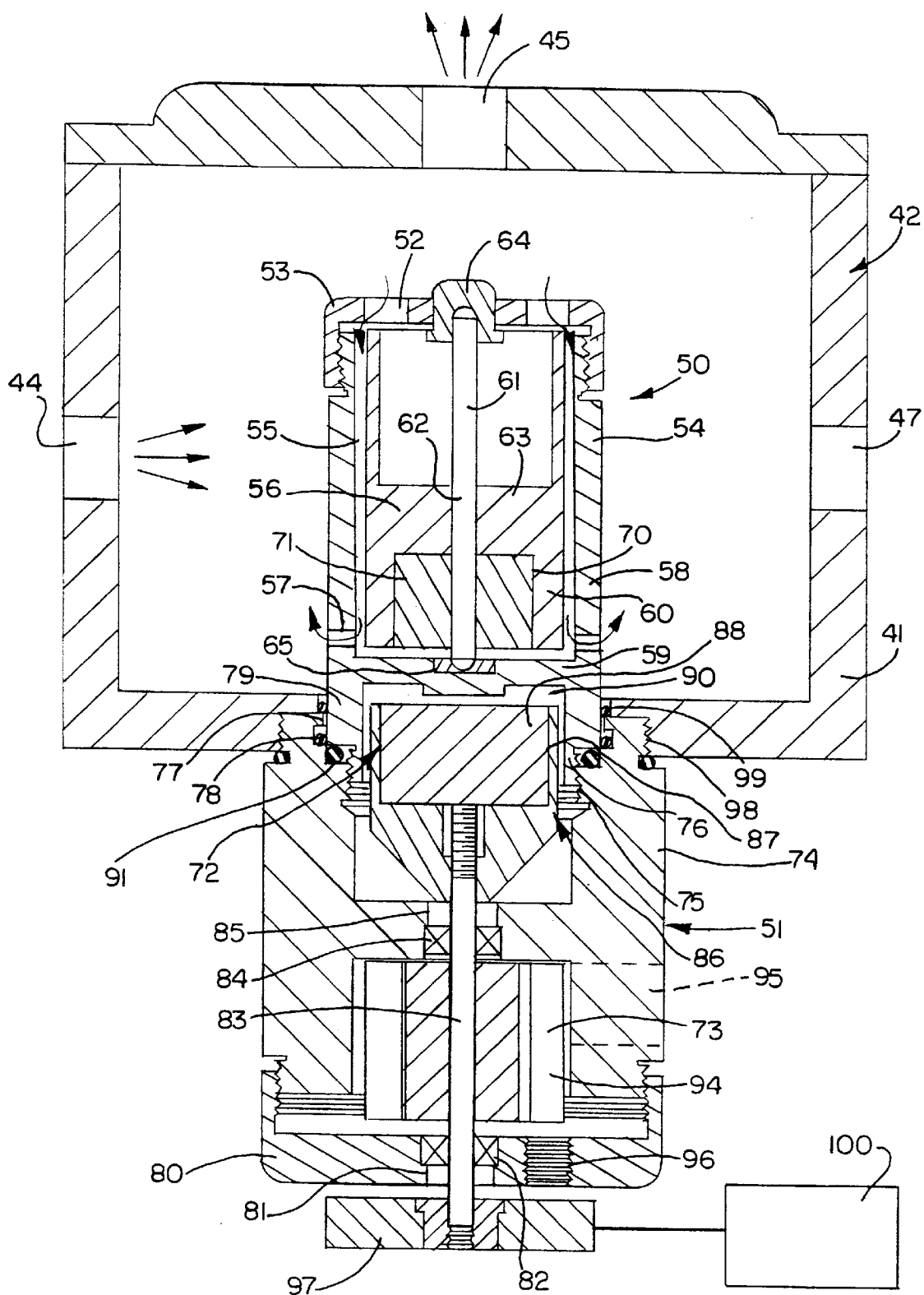
FIG. 2 is a longitudinal section through another form of viscometer according to this invention.

FIG. 2 shows another form of viscometer 50 in accordance with this invention for continuously monitoring fluid viscosity by monitoring the load imposed on an air motor 51 instead of a precision motor. In this embodiment, the fluid enters the viscometer through slots 52 in a cover or cap 53 on the outer end of a viscometer cup 54 and flows through an annular gap 55 between the bob 56 and cup 54 and out through a plurality of discrete circumferentially spaced openings 57 in the wall 58 of the cup near its closed end 59 that face a continuous wall 60 of the bob. During differential rotation of the bob and cup, these discrete openings 57 around the circumference of the cup coaxial to the rotating bob create a pressure differential causing fluid to be pumped through the viscometer that is a function of viscometer rotational speed and fluid viscosity.

In the embodiment shown in FIG. 2, the discrete openings 57 in the cup side wall 58 are located closely adjacent the closed end wall 59 of the cup to allow any debris or sediment within the fluid flowing through the viscometer to exit the cup through the openings.

The bob 56 is mounted for relative rotation within the cup 54 by means of a bob shaft 61 pressed into a coaxial bore 62 in a transverse wall 63 intermediate the ends of the bob. The bob shaft 61 extends beyond opposite ends of the bob into bronze inserts 64, 65 pressed into coaxial recesses in the cap 53 and cup end wall 59. Each bronze insert has a close tolerance hole with a half ball radius at the bottom for seated engagement by the ends of the bob shaft which have radiuses that are slightly smaller than the radius of the bronze inserts, whereby the bob will move like a gyro within the inserts with little effort required. Preferably, the end play between the bob shaft 61 and bearing inserts 64, 65 is no more than 0.010 inch, thus allowing the viscometer to operate in virtually any position.

At the inner end of the bob 56 is a cylindrical recess 70 containing the driven magnet 71 of a magnetic drive coupling 72 used to drive the bob by the air motor 51 as described hereafter. The driven magnet 71 is polarized north and south from one side to the other rather than the more typical top to bottom.

The air motor unit 51 that drives the viscometer bob includes an air rotor 73 mounted for rotation within a motor housing 74. At one end of the motor housing 74 is an internally threaded bore 75 for threaded engagement by an externally threaded inner end 76 of the viscometer cup 54. Coaxially spaced from the internal threads 75 is a larger diameter counterbore 77 in the motor housing containing a ring seal 78 for sealing engagement with a larger diameter cylindrical surface 79 on the viscometer cup 54.

Threadedly attached to the other end of the motor housing 74 is an end cap 80 containing a coaxial bore 81. Pressed into the bore 81 is a roller bearing 82 through which the rotor shaft 83 extends to stabilize the rotor 73. A second roller bearing 84 is pressed into a coaxial bore 85 in the motor housing 74 coaxially spaced from the end cap 80 to provide a slip fit for the rotor shaft.

Threadedly connected to the inner end of the rotor shaft 83 is a magnetic driver 86 containing a pocket 87 for receipt of the driving magnet 88 of the magnetic drive coupling 72. The pocket portion 87 of the magnetic driver 86 containing the driving magnet 88 extends into an annular recess 90 in the innermost end of the viscometer cup 54. The axial distance between the driving magnet 88 and driven magnet 71 of the magnetic drive coupling 72 is set by locating the rotor shaft 83 within the motor housing 74 and an internal shoulder 91 on the motor housing that the viscometer cup 54 locks against.

The motor housing 74 and end cap 80 as well as the rotor shaft 83 and magnetic driver 86 are desirably made of stainless steel, whereas the rotor 73 is desirably made of aluminum. Rotor 73 is provided with a plurality of circumferentially spaced panels 94. Regulated air pressure is directed through inlet and outlet ports 95 and 96 in the motor housing 74 in alignment with the rotor for driving the rotor and thus the viscometer bob 56 magnetically coupled thereto. Attached to the outer end of the rotor shaft 83 is a hub 97 with gear teeth for reading the RPMs of the rotor.

At the inner end of the rotor housing 74 are external threads 98 for threaded engagement within an opening 99 in the wall 41 of the diagnostics chamber 42 with the wet side of the viscometer 50 including the viscometer cup 54 and bob 56 extending into the fluid within the chamber. Differential bob/cup rotation urges fluid from the volume within the diagnostics chamber through slots 52 in the cup cap 53, then through the annular gap 55 between the bob and cup and out through the discrete openings 57 in the cup wall to the volume within the diagnostics chamber outside the cup.

Variations in fluid viscosity affect loading of the air motor 51 due to the change in drag between the relatively rotating bob 56 and cup 54. However, in this case, the changes in viscosity are translated into regulated air pressure and RPMs of the rotor 73 which are monitored by the electronics in the controller 100. Here again, these variations can be calibrated against known viscosities and can be programmed into the electronic control system 100 to make it possible to detect very small changes in viscosity.

Figure 3:
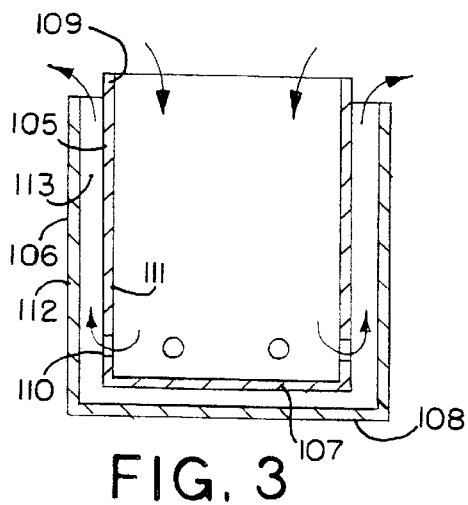
FIGS. 3 through 10 are schematic longitudinal sections through differently configured relatively rotating viscometer elements according to this invention.

If desired, the discrete openings used to create a pressure differential and cause fluid to be pumped through the viscometer during relative bob/cup rotation may be provided in the bob in lieu of the cup or in both the bob and cup. FIG. 3 schematically shows a bob 105 and cup 106 arrangement in which the bob 105 is closed at one end 107 adjacent the closed end 108 of the cup and is open at the other end 109, and has discrete circumferentially spaced openings 110 through the wall 111 of the bob near the closed end 107 and facing a continuous wall 112 of the cup. In this embodiment, differential bob/cup rotation urges fluid from a volume outside the bob (e.g., within the diagnostics chamber 42) through the bob 105 and out through the discrete openings 110 in the bob wall 111 and then through the annular gap 113 between the bob and cup and back into the volume outside the cup.

Figure 4:
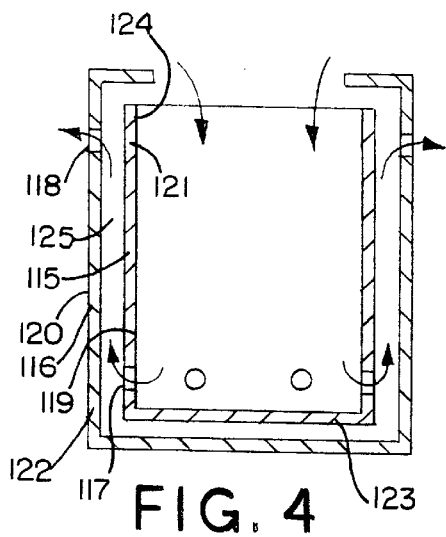
Figure 5:
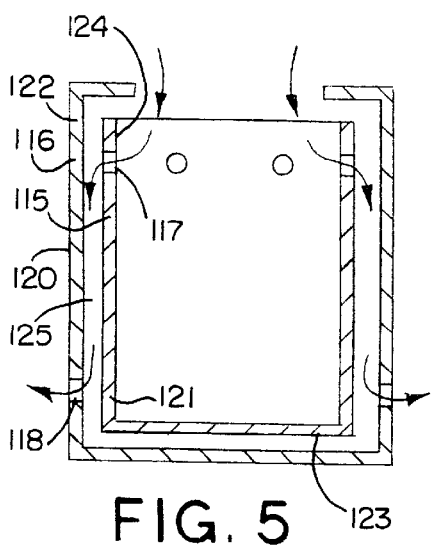

FIGS. 4 and 5 schematically show other bob/cup embodiments which are similar to the bob/cup arrangement shown in FIG. 3 except that in both FIGS. 4 and 5 the bob 115 and cup 116 have discrete circumferentially spaced radial openings 117, 118 through their respective walls 119, 120 in axially spaced apart relation from each other and facing a continuous wall 121, 122 of the other. In FIG. 4 the discrete openings 117 in the bob 115 are adjacent the closed end 123 of the bob and the discrete openings 118 in the cup 116 are near the open end 124 of the bob, whereas in FIG. 5 the discrete openings 117 in the bob are near the open end 124 of the bob and the discrete openings 118 in the cup are near the closed end 123 of the bob. In either case, differential bob/cup rotation urges fluid from a volume outside the bob through the bob, then through the discrete openings 117 in the wall of the bob and through the annular gap 125 between the bob and cup and out through the discrete openings 118 in the wall of the cup and return to the volume outside the cup.

Figure 6:
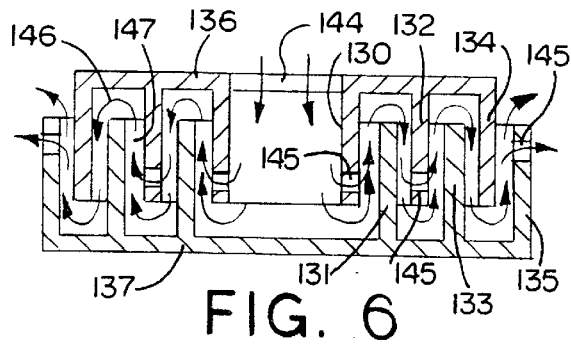
Figure 7:
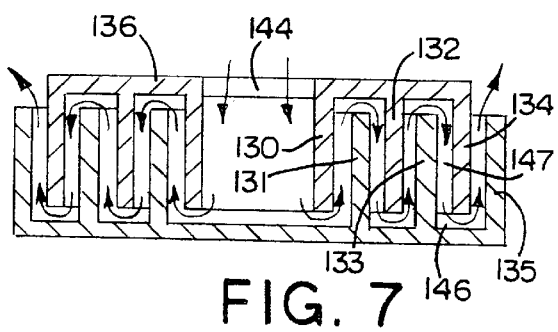

FIGS. 6 and 7 show two other bob/cup embodiments in accordance with this invention in which a series of alternate coaxial cylinders 130–135 of finite wall thickness are alternately supported by a pair of axially spaced end plates 136, 137. In this arrangement, cylinder 130 is the bob in the cup formed by the cylinder 131 and end plate 137. Cylinder 131 is the bob in the cup formed by cylinder 132 and end plate 136. Cylinder 132 is the bob in the cup formed by cylinder 133 and end plate 137. Cylinder 133 is the bob in the cup formed by cylinder 134 and end plate 136. Cylinder 134 is the bob in the cup formed by cylinder 135 and end plate 137. End plate 136 has a center opening 144 providing fluid communication between a volume of fluid outside end plate 136 (e.g., the diagnostics chamber 42 shown in FIGS. 1 and 2) and cylinder 130. In the FIG. 6 embodiment, discrete circumferentially spaced radial openings 145 are provided through the wall of at least one cylinder near its open end facing a continuous wall of the adjacent cylinder or cylinders. For example, if the openings 145 are through either of the inner or outermost cylinders 130 or 135, the openings 145 face only one adjacent cylindrical wall 131 or 134 whereas if the openings 145 are through any of the intermediate cylinders 131, 132 and 133, the openings 145 face two adjacent cylindrical walls. In the FIG. 7 embodiment, the cylinder of at least one bob/cup is located near the end plate of the adjacent cup/bob such that the separation 146 between the end of the one bob/cup cylinder and the end plate of the adjacent cup/bob is between one half to five times the gap 147 between adjacent cylinders.

In both embodiments shown in FIGS. 6 and 7, differential rotation of the end plates 136, 137 and thus the associated cylinders 130–135 urges fluid from a volume outside the end plate 136 (e.g., the diagnostics chamber 42 shown in FIGS. 1 and 2) through the center cylinder 130 and separations 146 between the bob/cup cylinders and opposed end plates (and in the case of the FIG. 6 embodiment through the circumferentially spaced openings 145 in the cylindrical wall of at least one bob/cup), then through the annular gaps 147 between adjacent bob/cup cylinders and out through the annular gap between the last of the bob/cup cylinders into the volume outside the outermost cylinder 135.

Figure 8:
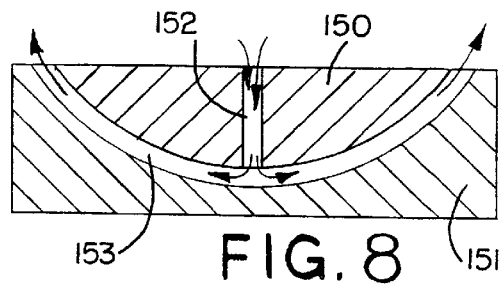
Figure 9:
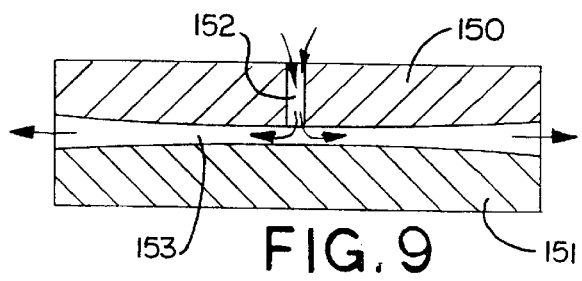
Figure 10:
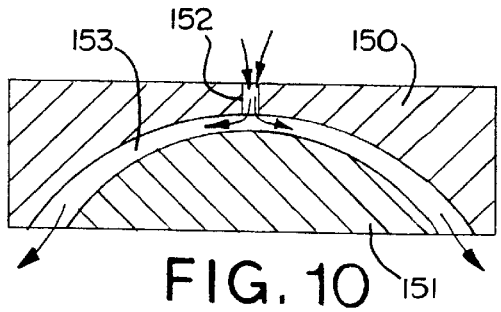

FIGS. 8 through 10 schematically show still other bob/cup embodiments in which the bobs 150 and cups 151 are axially symmetric but non-cylindrical. In each case the bobs 150 have a coaxial bore 152 all the way through the bobs. Also, the relative shapes of the bobs and cups are such that the gaps 153 there between remain the same as shown in FIG. 8 or increase as a function of radius from the common axis of the bobs and cups as shown in FIGS. 9 and 10 to facilitate pumping and removal of particulate. Differential bob/cup rotation urges fluid from a volume outside the bobs through the coaxial openings in the bobs and gaps between the bobs and cups and out into a volume outside the cups.

From the foregoing, it will be apparent that the various viscometers of the present invention include novel bob/cup configurations having discrete circumferentially spaced radial openings in the wall of one or both of the bob/cup facing a cylindrical surface on the other cup/bob or in which both ends of the bob are open and the axial separation between the end of the bob and adjacent cup bottom is between one half to five times the annular gap between the bob/cup to create a pressure differential during differential bob/cup rotation to cause fluid to be pumped through the viscometer. Thus, the viscometers are capable of maintaining a fluid flow through the viscometers that is a function of viscometer rotational speed and fluid viscosity, independent of any sources used to produce a fluid pressure differential. This self-pumping feature is also important when measuring low viscosity fluids that contain particulate, in that the pumping action keeps the particulate in suspension during normal use, and redisperses particulate should settling occur during shut down.

Although the invention has been shown and described with respect to certain preferred embodiments, it is obvious that equivalent alterations and modifications will occur to others skilled in the art upon the reading and understanding of the specification. The present invention includes all such equivalent alterations and modifications, and is limited only by the scope of the claims.

What is claimed is:

1. A viscometer for measuring or characterizing the stress required to shear a fluid at a given rate comprising a pair of members coaxially mounted for relative rotation wherein one of said members comprises a cup and the other of said members comprises a bob coaxially mounted within said cup with a separation between an inner end of said bob and a closed end of said cup that is between one half to five times the annular gap between said members, said bob having a longitudinal passage there through, whereby differential rotation of said bob and said cup causes fluid from a volume outside said bob to flow through said bob, through said separation between said bob and said cup and through said annular gap to a volume outside said cup, an annular gap between said members defining a flow path for the fluid, a driver for producing such differential rotation, means within said flow path for causing fluid to flow through said gap during such differential rotation that is a function of the differential rate of rotation between said members the viscosity of the fluid, and a sensor for measuring the torque or torque equivalent required to achieve such differential rotation between said members, and a pumping action of fluid through the viscometer.

2. The viscometer of claim 1 wherein said means for causing fluid to flow through said gap comprises a plurality of circumferentially spaced discrete openings in one of said members through which the fluid flows to create a differential pressure causing the fluid to be pumped through said gap.

3. The viscometer of claim 2 wherein said discrete openings extend through a wall of one of said members and face a continuous wall of the other of said members.

4. The viscometer of claim 2 wherein one of said members comprises a cup and the other of said members comprises a bob coaxially mounted within said cup, said bob having a closed end adjacent a closed end of said cup.

5. The viscometer of claim 4 wherein said discrete openings extend through a wall of said bob adjacent said closed end of said bob and face a continuous wall of said cup.

6. The viscometer of claim 4 wherein said discrete openings extend through a wall of said cup adjacent said closed end of said cup and face a continuous wall of said bob.

7. The viscometer of claim 4 wherein said discrete openings extend through both a wall of said bob and a wall of said cup.

8. The viscometer of claim 7 wherein said discrete openings through said wall of said bob are adjacent said closed end of said bob and face a continuous wall of said cup, and said discrete openings through said wall of said cup are near an open end of said bob and face a continuous wall of said cup.

9. The viscometer of claim 7 wherein said discrete openings through said wall of said cup are adjacent said closed end of said cup and face a continuous wall of said bob, and said discrete openings through said wall of said bob are axially spaced from said discrete openings through said wall of said cup and face a continuous wall of said cup.

10. The viscometer of claim 1 wherein said members are formed by coaxial cylinders on a pair of axially spaced end plates mounted for differential rotation, one of said end plates having a center opening providing fluid communication between a volume of fluid outside said one end plate and one of said cylinders.

11. The viscometer of claim 10 wherein each of said end plates has a plurality of alternate coaxial cylinders defining said gap there between.

12. The viscometer of claim 11 wherein said means for causing fluid to flow through said gap comprises a separation between at least one of said cylinders on one of said end plates and the other end plate that is between one half and five times said gap that creates a differential pressure causing the fluid to be pumped through said gap.

13. The viscometer of claim 11 wherein said means for causing fluid to flow through said gap comprises a plurality of circumferentially spaced discrete openings in at least one of said cylinders and facing a continuous wall of an adjacent cylinder through which the fluid flows creating a differential pressure causing the fluid to be pumped through said gap.

14. The viscometer of claim 1 wherein said members are axially symmetric but non-cylindrical, said members being shaped such that said annular gap increases as a function of the radius from a common axis of said members which creates a differential pressure causing fluid from a volume outside one of said members to flow through said one member and through said annular gap and into a volume outside the other of said members.

15. The viscometer of claim 1 wherein said members are axially symmetric but non-cylindrical, said members being shaped such that said annular gap remains the same as a function of the radius from a common axis of said members which creates a differential pressure causing fluid from a volume outside one of said members to flow through said one member and through said annular gap and into a volume outside the other of said members.

16. The viscometer of claim 1 wherein said driver comprises a motor, and a magnetic drive coupling between said motor and one of said members, the other of said members being relatively fixed, said magnetic drive coupling comprising a driving magnet rotatably driven by said motor, and a driven magnet driven by said driving magnet.

17. The viscometer of claim 16 wherein said other member comprises a cup, and said one member comprises a bob rotatably mounted within said cup, and said driving magnet surrounds said cup.

18. The viscometer of claim 17 wherein said driven magnet is carried by said bob within said cup.

19. The viscometer of claim 17 wherein said driven magnet forms said bob.

20. The viscometer of claim 16 wherein said other member comprises a cup fixedly mounted within a housing, said housing having a bore in coaxial alignment with an open end of said cup, and a hollow shaft rotatably mounted in said bore, said shaft extending into said cup, and said one member comprising a bob fixedly mounted on said shaft within said cup.

21. The viscometer of claim 1 wherein said one of said members comprises a cup having a closed end and an open end covered by a slotted cap, and the other of said members comprises a bob rotatably mounted on a bob shaft within said cup, said shaft having opposite ends received in bearing inserts in said cap and said closed end of said cup.

22. The viscometer of claim 1 wherein said one of said members comprises a cup, and the other of said members comprises a bob rotatably mounted within said cup, and said driver comprises an air motor, and a magnetic drive coupling between said motor and said bob, said magnetic drive coupling comprising a driving magnet rotatably driven by said air motor, and a driven magnet mounted in a recess in an inner end of said bob, said air motor including a motor housing containing a rotor through which regulated air pressure is supplied for driving said rotor and thus said bob through said magnetic drive coupling.

23. The viscometer of claim 21 wherein said cup has an externally threaded closed end for threaded receipt in an internally threaded bore in one end of said motor housing, and said one end of said motor housing has external threads for threaded engagement in an opening in a diagnostics chamber with said cup extending into said chamber.

* * * * *

UNITED STATES PATENT AND TRADEMARK OFFICE
Certificate

Patent No. 6,257,051 B1                                                               Patented: July 10, 2001

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Frederick P. Boyle, Kirtland, Ohio; Gary Garvin, Mentor, Ohio; Klaus-Werner Damm, Chagrin Falls, Ohio; Daniel H. Heath, Ravenna, Ohio; Herman F. George, Chardon, Ohio; Peter John Moore, Hampshire, England; Dale Hicks, Surrey, England; Terence Edward Robinson, Hampshire, England; and Patrick M. Lane, Willoughby, Ohio.

Signed and Sealed this Twentieth Day of November 2001.

HEZRON E. WILLIAMS
*Supervisory Patent Examiner*
Art Unit 2856